United States Patent [19]

Beissinger et al.

[11] Patent Number: 5,061,688
[45] Date of Patent: Oct. 29, 1991

[54] HEMOGLOBIN MULTIPLE EMULSION

[75] Inventors: Richard L. Beissinger, Oak Park; Darsh T. Wasan, Westmont; Lahksman R. Sehgal, Flossmoor; Arthur L. Rosen, Wilmette, all of Ill.

[73] Assignees: Illinois Institute of Technology, Chicago; Northfield Laboratories, Inc., Evanston, both of Ill.

[21] Appl. No.: 234,386
[22] Filed: Aug. 19, 1988
[51] Int. Cl.⁵ .................... A61K 9/113; A61K 37/14; B01J 13/00
[52] U.S. Cl. ........................................ 514/6; 252/312; 252/314; 514/832; 514/833; 514/938; 514/939; 514/941
[58] Field of Search .................... 252/312; 514/6, 832, 514/833, 938, 939, 941

[56] References Cited

U.S. PATENT DOCUMENTS

| | | | |
|---|---|---|---|
| 4,146,499 | 3/1979 | Rosano | 252/312 X |
| 4,461,717 | 7/1984 | Moore | 514/832 X |
| 4,569,784 | 2/1986 | Moore | 252/312 X |
| 4,590,086 | 5/1986 | Takahashi et al. | 252/312 X |
| 4,776,991 | 8/1986 | Farmer et al. | 264/4.3 |

FOREIGN PATENT DOCUMENTS 0038173 10/1981 European Pat. Off. .
0091183 2/1983 European Pat. Off. .

OTHER PUBLICATIONS

Szoka, Jr. et al., "Procedure for Preparation of Liposomes with Large Internal Aqueous Space and High Capture by Reverse-Phase Evaporation", Proc. Natl. Acad. Sci. USA, vol. 75, No. 9, pp. 4194–4198, Sep. 1978, Biochemistry.
Hackh's Chemical Dictionary, Fourth Edition, Revised and Edited by Julius Grant, McGraw-Hill Book Co., New York, 1969, pp. 240, 168 & 169.
Sehgal, L. R., Gould, S. A., Rosen, A. L., Moss, G. S.: Red Cell Appraisal of Red Cell Substituents: Hemoglobin Solution and Perfluorchemical Emulsions, Laboratory Medicine, 14:545, 1983.
Gould, S. A., Rosen, A. L., Sehgal, L. R., Moss, G. S.: Red Cell Substitutes: Hemoglobin Solution of Flurocarbon?, J. Trauma, 22:736, 1982.
Gould, S. A., Rosen, A. L., Sehgal, L. R., Moss, G. S.: Hemoglobin Solutions as Red Cell Substitutes, Trans. Am. Soc. Art. Int. Organs, 26:350, 1980.
Sehgal, L. R., Rosen, A. L., Gould, S. A., Moss, G. S.: Polymerized Pyridoxylated Hemoglobin: A Red Cell Substitute with Normal Oxygen Capacity, Surgery, 95:433, 1984.
Miller, I., Synthetic Block Substitutes: Where Are We and Where Do We Go From Here?, CRC, Crit. Rev. BioEng., 149–178, Dec. 1978.
T. Davis, W. Asher and H. Wallace, Artificial Red Cells with Crosslinked Hemoglobin Membranes, Applied Biochemistry and Biotechnology, vol. 10, 1984.
S. Matsumoto, Y. Kita, D. Yonezawa, An Attempt at Preparing Water-in-Oil-in-Water Multiple-Phase Emulsions, Journal of Colloid and Interface Science, vol. 57, No. 2, Nov. 1976.
S. Matsumoto, Y. Ueda, Y. Kita, D. Yonezawa, Preparation of Water-in-Olive Oil-in-Water Multiple-Phase Emulsions in an Eatable Form, Agric. Biol. Chem., 42 (4), 739–743, 1978.
P. E. Keipert, T. M. S. Chang, In Vivo Assessment of Pyridoxylated Crosslinked Polyhemoglobin as an Artificial Red Cell Substitute in Rats, vol. 29, pp. 329–333, Trans. Am. Soc. Artif. Intern. Organs, 1985.
P. E. Keipert, T. M. S. Chang, Pyridoxylated Polyhemoglobin as a Red Cell Substitute for Resuscitation of Lethal Hemorrhagic Shock in Conscious Rats, vol. 13 (1&2), pp. 1–15, Biomat. Med. Dev. Art. Org., 1985.

Primary Examiner—Richard D. Lovering
Attorney, Agent, or Firm—Speckman & Pauley

[57] ABSTRACT

A multiple emulsion of aqueous oxygen carrying material in oil in outer aqueous phase is suitable for provision of oxygen for oxygen transfer processes. A hemoglobin multiple emulsion in physiologically compatible oil in an outer aqueous saline solution is provided in sufficiently small droplet size to provide oxygen flow through blood vessels to desired body tissues or organs thereby providing a blood substitute. A process is provided wherein hemoglobin, a fragile material, is formulated into high hemoglobin content water-in-oil-in-water multiple emulsions while maintaining high yields and high oxygen exchange activity.

35 Claims, 2 Drawing Sheets

HEMOGLOBIN MULTIPLE EMULSION

BACKGROUND OF THE INVENTION

1. Field of the Invention

Hemoglobin multiple emulsion having specified properties is suitable for provision of oxygen as a blood substitute and other oxygen transfer processes. A double emulsion of aqueous high hemoglobin content in physiologically compatible mineral oil or vegetable oil in an outer aqueous saline solution is provided in sufficiently small droplet size to provide oxygen flow through blood vessels to desired body tissues or organs. A process is provided wherein hemoglobin, a fragile material, is formulated into high hemoglobin content water in oil in water multiple emulsions while maintaining high oxygen exchange activity necessary for the above uses.

2. Description of the Prior Art

It is important in many physiological and industrial applications to have available an oxygen carrying chemical for provision of oxygen to an oxygen depleted environment. One of the most important aspects is provision of an effective oxygen carrying blood substitute. In addition to emergency situations where there are not adequate supplies of whole blood, there are advantages in use of a synthetic blood substitute over the use of whole blood. For example, the efficiency of oxygenation by deficient blood flow in a tissue or an organ resulting from restriction of a blood vessel cannot be treated by use of whole blood, whereas blood substitutes of low bulk viscosity may deliver oxygen through constricted vessels, thereby preventing heart attacks and strokes caused by constriction of the arteries. Use of synthetic blood substitutes also eliminates transmission of blood borne infectious diseases, such as hepatitis and acquired immune deficiency syndrome. Other problems of intolerance or allergy to blood may be solved by synthetic blood substitutes.

An ideal synthetic blood substitute should have high oxygen carrying capacity and low oxygen affinity to permit loading of oxygen in the lungs and releasing of oxygen in the tissue; colloid osmotic pressure close to that of blood plasma; viscosity the same or less than that of whole blood; non-toxicity to the human body; histocompatibility, no antigenic affects; an adequate lifetime in the circulatory system to meet the desired needs for oxygen provision; relatively rapid metabolism or excretion of chemical agents; and adequate storage stability. To date, no blood substitutes have been fully approved for use in the United States of America.

One approach to provision of blood substitutes has been use of media with high passive oxygen solubility, primarily perfluorocarbon emulsions, which have been found to be unstable, have inadequate oxygen carrying capacity, and are toxic to the human. Problems with many perfluorocarbon emulsions have been high oxygen concentrations necessary due to the fluorocarbon emulsion carrying oxygen by passive solubility and the necessity to store the emulsion in the frozen state to retain stability.

The most promising present approaches involve use of chemical hemoglobin in various forms. Although stroma-free hemoglobin solutions have an adequate oxygen carrying capacity, they have high oxygen affinity, high colloid osmotic pressure, possible toxicity, and clearance from the cardiovascular circulation which is too rapid. One problem with stroma-free hemoglobin solutions has been that their oxygen affinity is much higher than that of normal hemoglobin in red blood cells and therefore oxygen is preferentially extracted from the cellular hemoglobin. Sehgal, L. R., Gould, S. A., Rosen, A. L., Moss, G. S.: Appraisal of Red Cell Substitutes: Hemoglobin Solution and Perfluorochemical Emulsions, Laboratory Medicine, 14:545, 1983; Gould, S. A., Rosen, A. L., Sehgal, L. R., Moss, G. S.: Red Cell Substitutes: Hemoglobin Solution or Fluorocarbon?, J. Trauma, 22:736, 1982; Gould, S. A., Rosen, A. L., Sehgal, L. R., Moss, G. S.: Hemoglobin Solutions as Red Cell Substitutes; Trans. Am. Soc. Art. Int. Organs, 26:350, 1980. Pyridoxylation followed by polymerization of stromo-free hemoglobin solutions has reduced many of the above problems except for high oxygen affinity and possibly toxicity. Also, the process generates some methemoglobin, which is a form of hemoglobin which cannot transfer oxygen. Sehgal, L. R., Rosen, A. L., Gould, S. A., Moss, G. S.: Polymerized Pyridoxylated Hemoglobin: A Red Cell Substitute with Normal Oxygen Capacity, Surgery, 95:433, 1984; Keipert, P. E., Chang, T. M. S.: Preparation and Invitro Characteristics of Pyridoxylated Polyhemoglobin as Blood Substitutes, Appl. Biochem. Biotechnol. 10:133, 1984.

Encapsulation of hemoglobin solution in a synthetic cell has been attempted by encapsulating hemoglobin solution within nylon membranes, cross-linked protein membranes, polyhemoglobin membranes and liposomes encapsulating hemoglobin in phospholipid vesicles. Miller, I., Synthetic Blood Substitutes: Where Are We and Where Do We Go From Here?, CRC, Crit. Rev. BioEng., 149–178, December 1978. Hemoglobin solution droplet encapsulation in a polymerized hemoglobin encapsulating membrane using glutaraldehyde as a crosslinking agent is described in "Artificial Red Cells with Crosslinked Hemoglobin Membranes", Thomas A. Davis, William J. Asher and Herbert W. Wallace, Applied Biochemistry and Biotechnology, Vol. 10, pgs. 123–132 (1984). The liposome encapsulated hemoglobin, although overcoming many of the problems encountered with other blood substitute products, are still too rapidly cleared from the circulatory system, are limited in oxygen carrying capacity, and have low encapsulation efficiencies, in the order of 10 to 20 percent. A method of scaled-up production of liposome-encapsulated hemoglobin described in allowed U.S. patent application Ser. No. 901,710, filed Aug. 29, 1986, now U.S. Pat. No. 4,776,991, overcomes some of the problems pointed out above.

Preparation of multiple emulsions of water in oil in water using non-ionic emulsifiers, deionized distilled water and liquid paraffin with mixing to form the water in oil emulsion and homogenizing to form the oil in water emulsion is taught by "An Attempt at Preparing Water-in-Oil-in-Water Multiple Phase Emulsions", Sachio Matsumoto, Yashiko Kita and Daizo Yonezawa, Journal of Colloid and Interface Science, Vol. 57, No. 2, pgs. 353–361 (1976). Water in olive oil in water emulsions were prepared using a mixed soy lecithin and Span 80 emulsifier which interact to form a viscoelastic film at the oil/water interface and sucrose-fatty acid ester at the outer water phase is taught by "Preparation of Water-in-Olive Oil Multiple-Phase Emulsions in an Eatable Form", Sachio Matsumoto, Yoshiro Ueda, Yoshiko Kito, and Daizo Yonezawa, Agric. Biol. Chem., 42, No. 4, pgs. 739–743 (1978).

SUMMARY OF THE INVENTION

This invention relates to a double liquid emulsion of an aqueous solution of an oxygen carrying material, such as hemoglobin, in oil in aqueous outer phase. The double liquid emulsion of this invention has a primary emulsifying agent to aid in the formation and maintenance of the primary emulsion of aqueous hemoglobin solution in oil. A secondary emulsifier is used in the formation and maintenance of the secondary emulsion of the primary emulsion in an aqueous outer phase. Thus, the primary emulsion may be made up of primary emulsion droplets each comprising individual droplets or a plurality of individual droplets of aqueous hemoglobin solution in the oil phase and the secondary emulsion is made up of secondary emulsion droplets each comprising individual droplets or a plurality of individual droplets of the primary emulsion suspended in the aqueous outer phase as shown schematically in FIG. 1.

The oil phase may comprise mineral or vegetable oils which provide satisfactory emulsion stability. Suitable vegetable oils may include; olive, safflower, sesame and soybean. Mineral oils are preferred, including: No. 40 white oil, Carnation light oil and Klearol light oil. Mixtures of these oils may be used.

In order to prepare the multiple emulsion of this invention, it is necessary to first prepare the primary emulsion and then in a separate process prepare the secondary emulsion. We have found that in preparing the primary emulsion it is necessary to first mix the components using a stirrer, such as a magnetic stirrer, followed by high shear mixing and cavitation through a microfluidizer. The secondary emulsion is separately prepared by stirring, such as by magnetic stirring, with the desired small size selection being achieved by filtration. We have found that high shear mixing is not suitable for formation of the secondary emulsion.

The multiple emulsions according to this invention, have the following properties:

|  | Broadest Suitable | Preferred |
| --- | --- | --- |
| Viscosity | 3–9 cp | 3–5 cp |
| Primary emulsion droplet size | up to 5 μm | up to 3 μm |
| Secondary emulsion droplet size after filtration | up to 10 μm | up to 8 μm |
| Yield | 85–99% | 95–99% |
| Oxygen carrying capacity | 7–20 vol. % | 10–20 vol. % |

The sizes of the primary emulsion and secondary emulsion droplets are preferably as small as consistent with good stability: over 50 percent of freshly prepared primary emulsion droplets being smaller than 0.5 micron and over 50 percent of freshly prepared secondary emulsion droplets being smaller than 4 microns. The emulsions used in this invention may be macro-emulsions or micro-emulsions.

BRIEF DESCRIPTION OF THE DRAWINGS

The above objects and advantages of this invention will become more clear upon reading preferred embodiments of the invention and reference to the drawing wherein.

DESCRIPTION OF PREFERRED EMBODIMENTS

Figure 1:
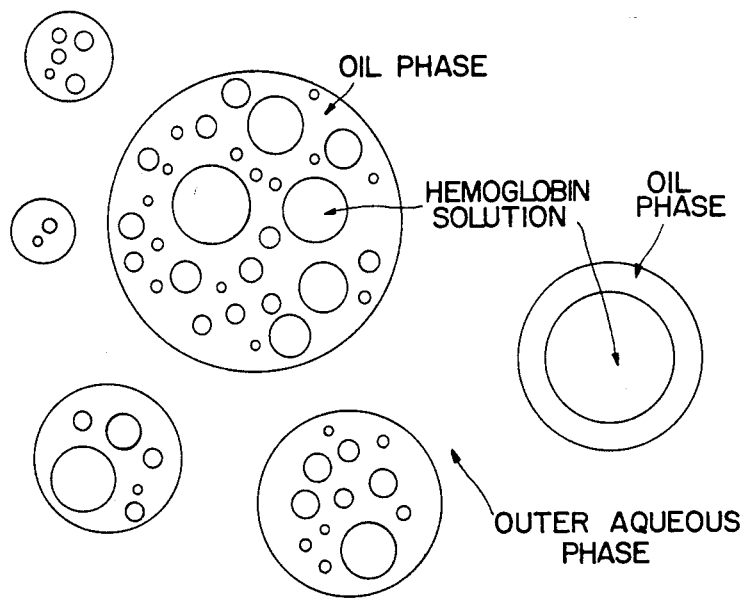
FIG. 1 is a schematic showing of an aqueous hemoglobin in oil in outer aqueous phase liquid double emulsion according to this invention.

An aqueous solution of any oxygen carrying material may be used in the primary emulsion portion of the multiple emulsion of this invention. Oxygen providing materials such as hemoglobin obtained from human blood or from bovine sources or modified hemoglobin such as pyridoxylated polyhemoglobin is suitable. The entire process is preferably carried out under refrigerated conditions of about 4° C. to about 8° C. to reduce formation of oxygen inactive methemoglobin. The process should also be carried out under aseptic conditions when the multiple emulsion is to be used as a blood substitute. All solutions used in preparing the multiple emulsion are filtered through a sterilizing filter during preparation of multiple emulsion for use as a blood substitute as well as the addition of antibiotics. The hemoglobin may be isolated from red blood cells by any suitable means known to the art and prepared in a relatively stroma-free aqueous hemoglobin solution concentrated from about 1 g % to about 35 g % and preferably from about 5 g % to about 35 g % hemoglobin. The aqueous hemoglobin solution, when used as a blood substitute may be dialyzed with phosphate buffered saline and may have added antibiotics, albumin, glucose, pyridoxol-5-phosphate (Vitamin A), and carbonic anhydrase.

Mineral or vegetable oils are suitably used to formulate the primary emulsion. Preferred mineral oils are No. 40 white oil, viscosity 4–5 cst @40° C., SG 0.804–0.820 @25° C., maximum pour point 2° C., and minimum flash point 135° C.; Carnation light mineral oil, viscosity 11–14 cst at 40° C., SG 0.837–0.953 at 25° C., pour point −7° C., and minimum flash point at 177° C., and Klearol light mineral oil, viscosity 7–10 cst at 40° C., SG 0.822–0.833, pour point −7° C., and minimum flash point at 138° C.; all obtained from Witco Chemical Corp. Preferred vegetable oils are sesame, olive and safflower vegetable oils obtained from Croda Inc., New York, N.Y. A primary emulsion emulsifier of polyoxyethylene alcohol, such as Brij 93, or sorbitan monooleate, such as Span 80, both obtained from ICI America Inc. is dissolved in the oil phase in an amount of 2 to 30 volume percent and preferably 5 to 15 volume percent, based upon the total primary emulsion.

For a primary emulsion using mineral oil, the aqueous hemoglobin solution in an amount of about 40 to about 90 volume percent, preferably about 60 to about 70 volume percent; mineral oil in an amount of about 8 to about 58 volume percent, preferably about 14 to about 25 volume percent; and primary emulsifying agent in an amount of about 2 to about 30 volume percent, preferably about 5 to about 15 volume percent are mixed. For a primary emulsion using vegetable oil, the aqueous hemoglobin solution in an amount of about 40 to about 90 volume percent, preferably about 40 to about 60 volume percent; vegetable oil in an amount of about 5 to about 30 volume percent, preferably about 20 to about 30 volume percent; and primary emulsifying agent in an amount of about 5 to about 30 volume percent, preferably about 20 to about 30 volume percent are mixed. The aqueous hemoglobin solution is preferably slowly added to the rapidly stirring oil phase and mixed, such as by use of a magnetic stirrer, for about 15 minutes to about 60 minutes and preferably about 25 minutes to about 35 minutes. The mixed primary emulsion was then subjected to high shear emulsification providing shear rates of about 100,000 to about 5,000,000 and preferably about 500,000 to about 1,000,000 $s^{-1}$ such as by using a microfluidizer at a pressure drop of about 1000 to about 3000, preferably about 1800 to about 2000 psi. More complete information regarding the microfluidizer is set forth in U.S. Pat. No. 4,533,254. The primary emulsion is filtered, such as by using a 5 micron hydrophilic polyvinylidene difluoride filter (Duropore, Millipore Corp.). Albumin may be added to the hemoglobin solution prior to emulsification in amounts of about 1 to about 5 g %, preferably about 2 to about 3 g %.

The primary emulsion of aqueous hemoglobin in mineral or vegetable oil to be suitable for preparation of the liquid multiple emulsion of this invention, should result in primary emulsion droplet diameters in the range of less than 5, and preferably less than 3, microns.

The outer aqueous phase of the multiple emulsion may be any aqueous liquid dependent upon the use to which the multiple emulsion is placed. To serve as a blood substitute, the outer aqueous phase is preferably isotonic phosphate buffered saline of a pH of about 7.4. A secondary emulsion emulsifier of polyoxyethylene fatty acid esters, such as Tween 40, Tween 60, Tween 80 (ICI America Inc.) or an ethylene oxide, such as Pluronic F68 (BASF Wyandotte Corp.), preferably Tween 60 or Pluronic F68, is dissolved in the outer aqueous phase in an amount of 0.25 to 2 weight percent and preferably 0.25 to 0.75 weight percent, based upon the total outer aqueous phase.

The primary emulsion, secondary emulsifying agent, and outer aqueous phase are mixed to form the secondary emulsion by dispersion, such as by a magnetic stirrer, for about 15 minutes to about 60 minutes, preferably about 25 minutes to about 35 minutes, to provide a uniform dispersion. It is preferred to add the primary emulsion to the outer phase in order to form the secondary emulsion. The final multiple emulsion suitably is in the proportion of about 10 to about 90, preferably about 35 to about 50 volume percent, of primary emulsion to about 10 to about 90, preferably about 50 to about 65, volume percent of outer aqueous phase of the secondary emulsion. The secondary emulsion may be filtered by any known technique to a final secondary emulsion product having desired secondary emulsion droplet sizes, both maximum and average size droplets. The droplets of the secondary emulsion prior to such filtration are about 20 to about 50 microns maximum size and about 10 to about 20 microns diameter average size and by filtering may readily be reduced to maximum droplet sizes of below 10 microns and average droplets of below 5 microns by passing up to three times through a filter such a 5 micron hydrophilic polyvinylidene difluoride filter resulting in a multiple emulsion suitable as a blood substitute.

Any desired water soluble additives may be added to the outer aqueous phase, such as albumin in amounts of 0.5 to 1.5 g % and dextran 0.5 to 1.0 g % which have been found to narrow size distribution and stabilize the multiple emulsion, and any other desired antibiotics like as mentioned above for hemoglobin solution.

The multiple emulsions produced in accordance with the process of this invention have been found to be very stable. The term "yield" as used herein expresses the amount of hemoglobin originally in the primary emulsion compared to the amount of hemoglobin leaked to the outer aqueous phase. Following preparation, the yield of the multiple emulsions has been found to be about 99 percent prior to filtering and after three filter passes through a 5 micron filter reduced to above 97 percent. The yield decreases during storage, but has been found to be above 85 percent following 23 days of storage under refrigerated conditions. Droplet sizes of the multiple emulsion increase with storage at refrigerated temperatures, for example, from a fresh average size of 3.8 microns to about 10 microns at 16 days and 15 microns at 23 days. Size distribution similar to the freshly prepared double emulsion can be obtained by one to three filtrations through a 5 micron filter as used in the original preparation. Oxygen carrying capacity of the multiple emulsion provides an oxygen content of about 14 ml $O_2$ per 100 ml of multiple emulsion and decreases to about 10 after 23 days of storage.

While the multiple emulsions of this invention may be used for various oxygen provision systems, an important aspect of this invention is the suitability of the multiple emulsions for use as a blood substitute. The droplet sizes of the multiple emulsion are suitable for use in a cardiovascular system. The steady shear viscosity of the multiple emulsion over the shear rate range expected in the cardiovascular system is about the same as that of whole blood and exposing the multiple emulsion to the shear rate range noted results in negligible change in yield, that is, negligible release of hemoglobin solution to the outer phase of the multiple emulsion. The oxygen carrying capacity of the multiple emulsion of this invention is similar to that of blood. From these properties and the physiological compatibility of an outer phosphate buffered saline aqueous phase, it would be expected that the multiple emulsions would be suitable for use as blood substitutes. As shown in the specific examples, multiple emulsions prepared according to this invention do not show acute toxicity when injected into mice as blood substitutes. The hemoglobin multiple emulsions of this invention may also be useful in the oxygenated preservation of donated body organs, as the oxygen exchange fluid in blood oxygenators, and the oxygen supplier in mammalian cell cultures.

The following specific Examples are set forth in detail to afford a better understanding of the invention, but should not be considered as limiting the invention.

EXAMPLE I

Figure 2:
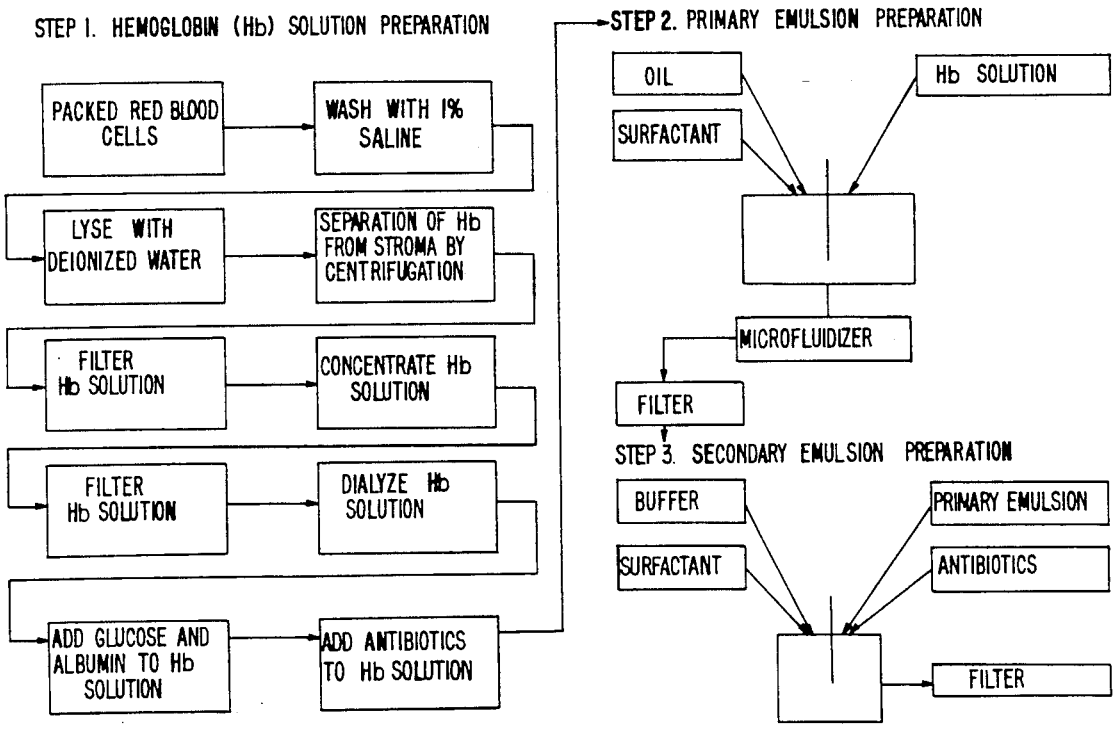
FIG. 2 is a simplified diagram of the steps of a process according to this invention.

A hemoglobin double emulsion was prepared by first preparing a hemoglobin in No. 40 white mineral oil primary emulsion followed by preparing a secondary emulsion of the primary emulsion in an aqueous phosphate buffered saline solution. FIG. 2 outlines the process followed in this Example.

A hemoglobin saline solution was prepared by washing red blood cells with 1.0 weight percent sodium chloride in deionized water at a volume ratio of 1:1 by gently mixing followed by centrifugation at 4000×g for ten minutes in a refrigerated centrifuge. After centrifugation, the buffy coat and supernatant were discarded and the washing procedure repeated until the supernatant was clear, usually 1 to 3 times. After washing, the packed red blood cells were lysed by dilution with 4 to 5 volumes of deionized water and the resulting mixture agitated for 12 hours using a magnetic stirrer in a refrigerator. The stroma, mainly red blood cell membrane fragments, were removed by centrifugation at 30,000×g for 30 minutes. The supernatant hemoglobin solution was removed and concentrated in a Minitan (Millipore Corp., Bedford, Mass.) cross flow ultrafiltration system using eight polysulfone 30,000 nominal molecular weight filter packets, the solution maintained in an ice bath during the entire concentration process to reduce the formation of methemoglobin. The concentration procedure was continued until the cross filtration flow rate had to be drastically reduced in order not to exceed the maximum recommended back pressure of the ultrafiltration system. The hemoglobin solution following concentration was up to 35 g %, 35 grams hemoglobin per 100 ml solution. The hemoglobin concentrate was dialyzed against 30 mM phosphate buffered saline to provide desired osmotic equilibrium with the outer aqueous phase. The pH of the phosphate buffer was adjusted as necessary, from 7.4 to 8.0, to assure that the pH of the dialyzed hemoglobin solution was about 7.4. The dialyzed hemoglobin solution was centrifuged at 30,000×g for 30 minutes and then filtered using 0.20 micron sterilizing filters (Fisher Chem. Co.) to remove any stroma material that precipitated due to the pH adjustment. Antibiotics were added to the hemoglobin solution to provide on a liter basis, penicillin—5000 units, Gentamicin—40 mg, Polymyxin—2500 units, and Streptomycin—50 mg. Also, the addition of human albumin and glucose resulted in 2.5 g % and 3.5 g % solutions, respectively.

The primary hemoglobin in oil emulsion was prepared using a magnetic stirring table by slowly adding the above prepared hemoglobin solution to a vigorously stirred white mineral oil No. 40 (Witco Chemical Corp.) containing 15 weight percent polyoxyethylene alcohol surfactant Brij 93 (ICI Americas Inc.). Slow addition of the hemoglobin solution to the vigorously stirred oil phase achieved high loading of the aqueous phase, 60 volume percent loading of hemoglobin solution in the oil phase. The hemoglobin-oil mixture was subjected to high energy emulsification under refrigerated conditions using an M 110 Microfluidizer Model BO4 with D-20 inserts (Microfluidics Corp.) at a pressure drop of 2000 psi with shear of about $1 \times 10^6 s^{-1}$ to achieve small multiple emulsion droplets and to increase the stability of the primary emulsion. The primary emulsion was then filtered using a 5 micron hydrophilic polyvinylidene difluoride filter (Duropore, Millipore Corp.).

The outer aqueous phase of the multiple emulsion was isotonic phosphate buffered saline of pH 7.4, selected for its physiological compatibility, to which was added 0.5 g % surfactant polyoxyethylene fatty acid esters Tween 60 (ICI America Inc.), 1 g % albumin and 0.5 g % dextran (62,400 MW, Sigma Chemical Company).

The above prepared primary hemoglobin in oil emulsion was then dispersed in the above prepared outer aqueous phase at a 1:1 volume ratio by mixing for 30 minutes with a magnetic stirrer. The multiple emulsion was filtered 3 times to reduce the maximum droplet size to below 10 microns and the average size of the droplets to below five microns by filtering through a 5 micron hydrophilic polyvinylidene difluoride filter (Duropore, Millipore Corp.) into a collection flask. The filtration was carried out under a slight vacuum of 25 kPa obtained by water aspiration which provided a filtration rate of about 5 ml per minute. When the multiple emulsion was prepared in a manner suitable for blood substitutes, all solutions used in the preparation of the multiple emulsion were sterilized by passage through a 0.2 micron filter.

Variation of pressure drop of the microfluidizer between 1000 and 3000 psia in preparation of the primary emulsion resulted in yields greater than 85 percent, peaking at 1800–2000 psia at 98 percent.

EXAMPLE II

A hemoglobin double emulsion was prepared as in Example I except that sesame vegetable oil was used in the primary emulsion. The aqueous hemoglobin solution containing 35 g % hemoglobin, and 3 g % human albumin was slowly (1 ml/min) added to the rapidly stirred oil phase which contained 50 weight percent Span 80, on basis oil phase, at a volume ratio of 40 volume percent, hemoglobin solution to 60 volume percent sesame oil for about 40 minutes and then subjected to high energy emulsification as described in Example I. The primary emulsion of aqueous hemoglobin in sesame oil was then dispersed in the outer aqueous phase of isotonic phosphate buffered saline which contained 1.0 weight percent human albumin, 0.5 weight percent dextran and 0.5 weight percent Pluronic F68 at a 1:1 volume ratio by mixing with low speed stirring for about 5 minutes. The multiple emulsion was filtered three times through a 5 micron filter to reduce the maximum droplet size to below 1μ and average droplet size to below 4μ.

EXAMPLE III

Samples of freshly prepared multiple emulsion prepared as described in Example I were diluted with outer aqueous phase and placed in a Howard Cell (Rascher & Betzold Inc., Chicago, Ill.) and photographed through a MicrOmaster Phase Contrast Microscope (Fisher Scientific Inc.) using an Olympus OM1 camera. Droplet sizes were measured from the negatives with an MOP-3 semi-automatic image analyzer (Carl Zeiss Inc.) The primary emulsion maximum droplet diameters were less than 1.5 microns with an average size of less than 0.5 micron. Following 5 days storage at 4° C. the maximum and average primary emulsion droplet diameters were 2.5 and 0.5, respectively. The size distribution of the primary emulsion droplets were found to be narrowed and stabilized with time by the addition of the albumin.

The maximum and average multiple emulsion droplet sizes were about 7 and 3.8 microns, respectively, for fresh emulsions; 10 and 4.8 microns, respectively, for 4 day old emulsions; 15 and 10 microns, respectively, for 15 day old emulsions; and 20 and 15 microns, respectively, for 23 day old emulsions, all maintained at 5° C. The albumin added to the outer aqueous phase resulted in decreased droplet size and significantly decreased droplet growth during storage. It was also found that the number of filter passes using the 5 micron filter was important. A second filter pass resulted in reducing the maximum size from about 35 to about 15 microns and a third pass reduced the maximum size to about 7 microns.

EXAMPLE IV

The yield, expressed by the amount of hemoglobin encapsulated in the primary emulsion compared to the amount leaked to the outer phase, was measured using the multiple emulsion prepared in Example I. The number of filter passes using the 5 micron filter reduced the yield from just below 99 percent prior to filtering to above 97 percent after three filter passes. The yield of the multiple emulsion during storage decreases, but after 7 days of storage at 5° C. was measured to be above 91 percent and after 23 days of storage at 5° C. was measured to be above 85 percent.

EXAMPLE V

The bulk viscosity of the multiple emulsion prepared in Example I was measured with a Wells-Brookfield Syncro-Lectric Microviscometer, Model LVT equipped with a 0.8° cone Model CP-40 (Brookfield Engineering Laboratories, Inc., Stoughton, Mass.) and with a Weissenberg Rheogoniometer Model R16/R19 equipped with a 10 cm 0.3° cone and plate, platen system. The steady shear viscosity of the multiple emulsion varied from about 5 cp at a shear rate of 50 $s^{-1}$ to 3.5 cp at a shear rate of 500 $s^{-1}$. This approximates the shear rate of whole blood in a cardiovascular system. Under such shear rates, the yield remained about constant and the shear rate had little effect on size distribution of the multiple emulsion droplets between shear rates of 45 $s^{-1}$ and 450 $s^{-1}$.

The steady shear viscosity of the multiple emulsion prepared in Example II was 3 cp.

EXAMPLE VI

The oxygen carrying capacity, that is the oxygen content, of the multiple emulsion prepared in Example I was measured using a modification of Neville's biotonometry method (Neville, J. R. *J. applied Physiology*, 37: 967, 1974) in a Warberg manometer (Fisher Scientific, Itasca, Ill.). Freshly prepared emulsion was measured to be about 14 ml $O_2$/100 ml multiple emulsion sample falling to about 10 ml $O_2$/100 ml multiple emulsion following 23 days of storage at 5° C.

The freshly prepared emulsion of Example II had an oxygen content of 10 ml $O_2$/100 ml multiple emulsion.

EXAMPLE VII

Figure 3:
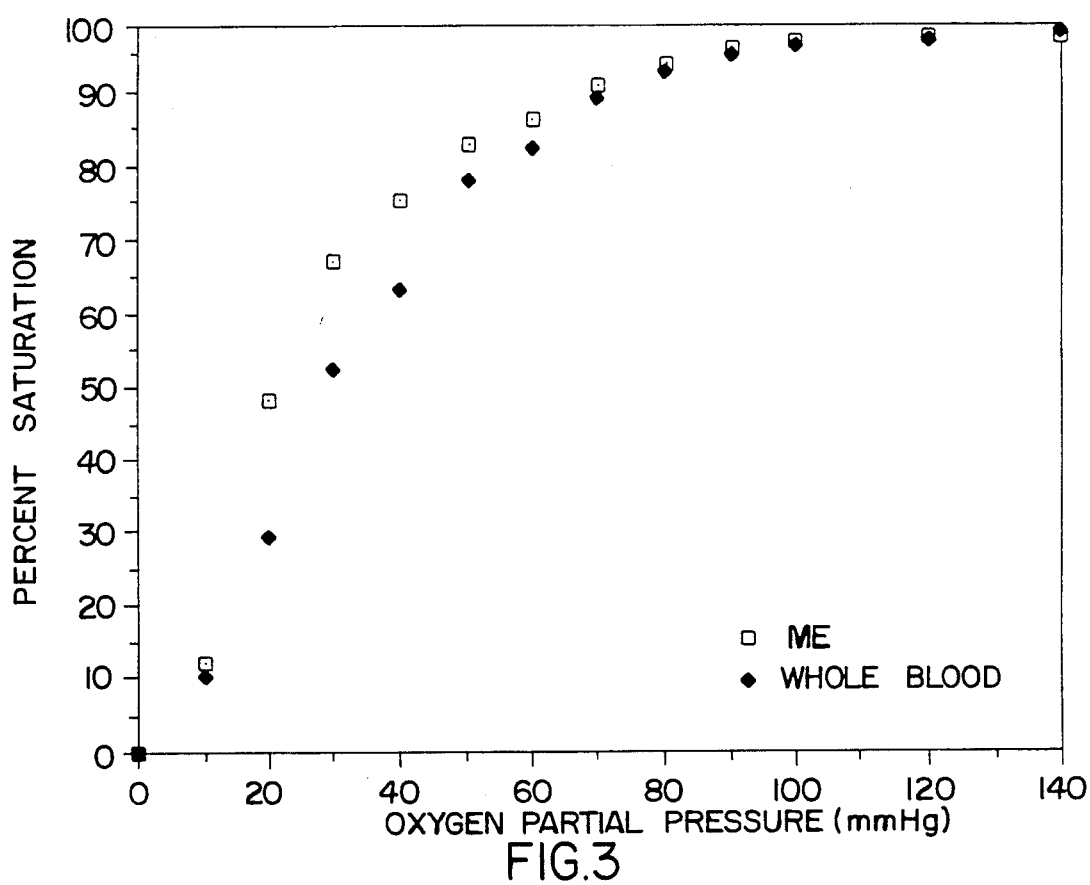
FIG. 3 is a graph showing the oxygen dissociation of a hemoglobin in oil in outer aqueous phase liquid multiple emulsion (ME) of this invention compared to whole blood.

A multiple emulsion was prepared in the manner described in Example I for use as a blood substitute except that the primary emulsion also contained pyridoxal-5-phosphate P-5-P (Sigma Chemical Company) at a molar ratio twice that of hemoglobin. P-5-P reduced the oxygen affinity to a $P_{50}$ value of 20 mm Hg compared to a measured $P_{50}$ value of 26 mm Hg for whole blood. The measurements were made at pH 7.35, $P_{CO}$ of Omm Hg, and temperature of 37° C. The oxyhemoglobin dissociation curve was measured using the modified biotonometry method and the results shown in FIG. 3 suggest a cooperativity similar to that of whole blood.

EXAMPLE VIII

A multiple emulsion was prepared in the manner described in Example I except that the primary emulsion contained 32.8 g % hemoglobin solution and the primary emulsion contained carnation white mineral oil and made up 30 volume percent of the multiple emulsion. 0.55 ccs of this multiple emulsion was injected into four mice. All the animals survived and continued to exhibit a healthy appearance for up to several days after the injections.

Another multiple emulsion was similarly made up containing 35 volume percent primary emulsion and 1.0 cc was administered to three mice, all of which survived and appeared healthy for up to several days following injection.

A multiple emulsion was made up as described immediately above wherein the primary emulsion made up 50 volume percent of the multiple emulsion. This emulsion was injected with a 0.5 cc amount into five mice. All the animals survived and continued to appear healthy for up to several days after the injections.

All the above tests indicate no acute toxicity of the hemoglobin multiple emulsion using mineral oil occurred in these mice.

EXAMPLE IX

A multiple emulsion was prepared in a manner described in Example VIII except that sesame vegetable oil as described in Example II was used instead of mineral oil. The primary emulsion contained 35 g % hemoglobin solution. The multiple emulsion contained 50 percent primary emulsion and 50 percent outer aqueous phase. 0.5 and 1.0 cc of this multiple emulsion was injected into two mice, both of which survived and continued to appear healthy for several days.

The above tests indicate no acute toxicity of the hemoglobin multiple emulsion using sesame oil occurred in these mice.

EXAMPLE X

Figure 4:
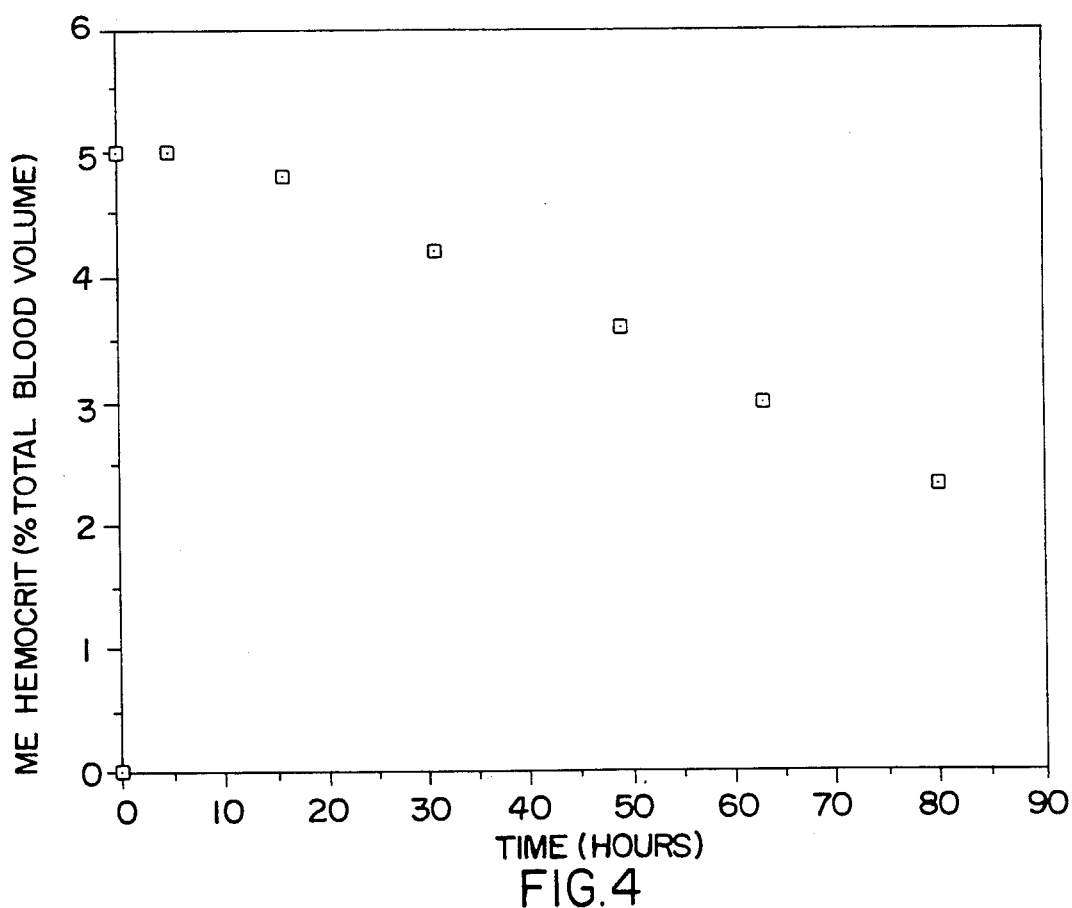
FIG. 4 is a graph showing the half-life of a hemoglobin in oil in outer aqueous phase liquid double emulsion of this invention in mice.

A multiple emulsion was prepared in a manner described in Example VIII with 35 volume percent primary emulsion for use as a blood substitute and was injected into five mice. Immediately following the injection step, a blood sample was collected in a microhematocrit tube. The multiple emulsion measured, after a 10 minute centrifugation, 5 volume percent of the animal's total blood volume. As shown in FIG. 4, the multiple emulsion dropped to 2 volume percent of the animal's total blood volume after 80 hours of circulation in the mice. Circulation half-life of the multiple emulsion in mice was determined to be about 70 hours.

EXAMPLE XI

A multiple emulsion was prepared in a manner described in Example VIII with 50 volume percent primary emulsion for use as a blood substitute. When mixed with platelet-rich plasma, no decrease in single platelets was observed.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An oxygen carrying multiple liquid emulsion comprising a primary emulsion comprising aqueous solution of oxygen carrying material in oil selected from the group consisting of mineral oil, vegetable oil and mixtures thereof, emulsified with a primary emulsifier having primary emulsion droplet sizes of up to about 5 microns and a secondary emulsion comprising said primary emulsion in an outer aqueous phase emulsified with a secondary emulsifier having secondary emulsion droplet sizes up to about 10 microns, said multiple emulsion having a viscosity of about 3 to about 9 cp, yield about 85 to about 99 percent, and oxygen carrying capacity about 7 to about 20 volume percent.

2. An oxygen carrying multiple emulsion according to claim 1 wherein said oxygen carrying material is hemoglobin.

3. An oxygen carrying multiple emulsion according to claim 1 wherein said oil is mineral oil.

4. An oxygen carrying multiple emulsion according to claim 3 wherein said mineral oil is selected from the group consisting of No. 40 white oil, Carnation light oil, Klearol light oil, and mixtures thereof.

5. An oxygen carrying multiple emulsion according to claim 3 wherein said primary emulsion comprises about 40 to about 90 volume percent aqueous hemoglobin, about 8 to about 58 volume percent said oil, and about 2 to about 30 volume percent said primary emulsifier.

6. An oxygen carrying multiple emulsion according to claim 3 wherein said primary emulsion comprises about 60 to about 70 volume percent aqueous hemoglobin, about 14 to about 25 volume percent said oil, and about 5 to about 15 volume percent said primary emulsifier.

7. An oxygen carrying multiple emulsion according to claim 1 wherein said oil is vegetable oil.

8. An oxygen carrying multiple emulsion according to claim 7 wherein said vegetable oil is selected from the group consisting of olive, safflower, sesame, soybean, and mixtures thereof.

9. An oxygen carrying multiple emulsion according to claim 7 wherein said primary emulsion comprises about 40 to about 90 volume percent aqueous hemoglobin, about 5 to about 30 volume percent said oil, and about 5 to about 30 volume percent said primary emulsifier.

10. An oxygen carrying multiple emulsion according to claim 7 wherein said primary emulsion comprises about 40 to about 60 volume percent aqueous hemoglobin, about 20 to about 30 volume percent said oil, and about 20 to about 30 volume percent said primary emulsifier.

11. An oxygen carrying multiple emulsion according to claim 1 wherein said primary emulsifier is selected from the group consisting of polyoxyethylene alcohol and sorbitan monooleate.

12. An oxygen carrying multiple emulsion according to claim 11 wherein said primary emulsifier is selected from the group consisting of Brij 93 and Span 80.

13. An oxygen carrying multiple emulsion according to claim 1 wherein said primary emulsion droplet sizes are up to about 3 microns.

14. An oxygen carrying multiple emulsion according to claim 1 wherein said secondary emulsifier is selected from the group consisting of Tween 40, Tween 60, Tween 80, and Pluronic F68.

15. An oxygen carrying multiple emulsion according to claim 1 wherein said secondary emulsion droplet sizes are up to about 8 microns.

16. An oxygen carrying multiple emulsion according to claim 1 wherein said multiple emulsion comprises about 10 to about 90 volume percent said primary emulsion, about 10 to about 90 volume percent said outer aqueous phase, and about 0.25 to about 2 weight percent said secondary emulsifier.

17. An oxygen carrying multiple emulsion according to claim 1 wherein said multiple emulsion comprises about 35 to about 50 volume percent said primary emulsion, about 50 to about 65 volume percent said outer aqueous phase, and about 0.25 to about 0.75 weight percent said secondary emulsifier.

18. An oxygen carrying multiple emulsion according to claim 1 wherein said yield is about 95 to about 99 percent.

19. An oxygen carrying multiple emulsion according to claim 1 wherein said oxygen carrying capacity is about 10 to about 20 volume percent.

20. An oxygen carrying multiple emulsion according to claim 1 wherein said oxygen carrying material is hemoglobin, said oil is mineral oil selected from the group consisting of No. 40 white oil, Carnation light oil, Klearol light oil, and mixtures thereof, said primary emulsifier is selected from the group consisting of Brij 93 and Span 80, said primary emulsion comprises about 40 to about 90 volume percent aqueous hemoglobin, about 8 to about 58 volume percent said mineral oil, and about 2 to about 30 volume percent said primary emulsifier, said secondary emulsifier is selected from the group consisting of Tween 40, Tween 60, Tween 80, and Pluronic F68, said multiple emulsion comprises about 10 to about 90 volume percent said primary emulsion, about 10 to about 90 volume percent said outer aqueous phase, and about 0.25 to about 2 weight percent said secondary emulsifier, said yield is about 95 to about 99 percent, and said oxygen carrying capacity is about 10 to about 20 volume percent.

21. An oxygen carrying multiple emulsion according to claim 1 wherein said oxygen carrying material is hemoglobin, said oil is vegetable oil selected from the group consisting of olive, safflower, sesame, soybean and mixtures thereof, said primary emulsifier is selected from the group consisting of Brij 93 and Span 80, said primary emulsion comprises about 40 to about 90 volume percent aqueous hemoglobin, about 5 to about 30 volume percent said vegetable oil, and about 5 to about 30 volume percent said primary emulsifier, said secondary emulsifier is selected from the group consisting of Tween 40, Tween 60, Tween 80, and Pluronic F68, said multiple emulsion comprises about 10 to about 90 volume percent said primary emulsion, about 10 to about 90 volume percent said outer aqueous phase, and about 0.25 to about 2 weight percent said secondary emulsifier, said yield is about 95 to about 99 percent, and said oxygen carrying capacity is about 10 to about 20 volume percent.

22. A blood substitute comprising a sterile oxygen carrying multiple liquid emulsion comprising a primary emulsion comprising aqueous solution of oxygen carrying material in oil selected from the group consisting of mineral oil, vegetable oil and mixtures thereof, emulsified with a primary emulsifier having primary emulsion droplet sizes of up to about 5 microns and a secondary emulsion comprising said primary emulsion in an outer aqueous phase emulsified with a secondary emulsifier having secondary emulsion droplet sizes up to about 10 microns, said multiple emulsion having a viscosity of about 3 to about 9 cp, yield about 85 to about 99 percent, and oxygen carrying capacity about 7 to about 20 volume percent.

23. A blood substitute according to claim 22 wherein said oxygen carrying material is hemoglobin.

24. A blood substitute according to claim 22 wherein said oil is mineral oil selected from the group consisting of No. 40 white oil, Carnation light oil, Klearol light oil, and mixtures thereof.

25. A blood substitute according to claim 24 wherein said primary emulsion comprises about 40 to about 90 volume percent aqueous hemoglobin, about 8 to about 58 volume percent said oil, and about 2 to about 30 volume percent said primary emulsifier.

26. A blood substitute according to claim 22 wherein said oil is vegetable oil selected from the group consisting of olive, safflower, sesame, soybean, and mixtures thereof.

27. A blood substitute according to claim 26 wherein said primary emulsion comprises about 40 to about 90 volume percent aqueous hemoglobin, about 5 to about 30 volume percent said oil, and about 5 to about 30 volume percent said primary emulsifier.

28. A blood substitute according to claim 22 wherein said primary emulsifier is selected from the group consisting of Brij 93 and Span 80.

29. A blood substitute according to claim 22 wherein said primary emulsion droplet sizes are up to about 3 microns.

30. A blood substitute according to claim 22 wherein said secondary emulsifier is selected from the group consisting of Tween 40, Tween 60, Tween 80, and Pluronic F68.

31. A blood substitute according to claim 22 wherein said multiple emulsion comprises about 10 to about 90 volume percent said primary emulsion, about 10 to about 90 volume percent said outer aqueous phase, and about 0.25 to about 2 weight percent said secondary emulsifier.

32. A blood substitute according to claim 22 wherein said multiple emulsion comprises about 35 to about 50 volume percent said primary emulsion, about 50 to about 65 volume percent said outer aqueous phase, and about 0.25 to about 0.75 weight percent said secondary emulsifier.

33. A blood substitute according to claim 22 wherein said yield is about 95 to about 99 percent.

34. A blood substitute according to claim 22 wherein said oxygen carrying material is hemoglobin, said oil is mineral oil selected from the group consisting of No. 40 white oil, Carnation light oil, Klearol light oil, and mixtures thereof, said primary emulsifier is selected from the group consisting of Brij 93 and Span 80, said primary emulsion comprises about 40 to about 90 volume percent aqueous hemoglobin, about 8 to about 58 volume percent said mineral oil, and about 2 to about 30 volume percent said primary emulsifier, said secondary emulsifier is selected from the group consisting of Tween 40, Tween 60, Tween 80, and Pluronic F68, said multiple emulsion comprises about 10 to about 90 volume percent said primary emulsion, about 10 to about 90 volume percent said outer aqueous phase, and about 0.25 to about 2 weight percent said secondary emulsifier, said yield is about 95 to about 99 percent, and said oxygen carrying capacity is about 10 to about 20 volume percent.

35. A blood substitute according to claim 22 wherein said oxygen carrying material is hemoglobin, said oil is vegetable oil selected from the group consisting of olive, safflower, sesame, soybean, and mixtures thereof, said primary emulsifier is selected from the group consisting of Brij 93 and Span 80, said primary emulsion comprises about 40 to about 90 volume percent aqueous hemoglobin, about 5 to about 30 volume percent said vegetable oil, and about 5 to about 30 volume percent said primary emulsifier, said secondary emulsifier is selected from the group consisting of Tween 40, Tween 60, Tween 80, and Pluronic F68, said multiple emulsion comprises about 10 to about 90 volume percent said primary emulsion, about 10 to about 90 volume percent said outer aqueous phase, and about 0.25 to about 2 weight percent said secondary emulsifier, said yield is about 95 to about 99 percent, and said oxygen carrying capacity is about 10 to about 20 volume percent.

* * * * *